(12) United States Patent
Magno

(10) Patent No.: US 12,349,934 B2
(45) Date of Patent: Jul. 8, 2025

(54) MEDICAL DEVICE WITH REMOVABLE MOTOR

(71) Applicant: GYRUS ACMI, INC., Westborough, MA (US)

(72) Inventor: Joey Magno, Dudley, MA (US)

(73) Assignee: GYRUS ACMI, INC., Westborough, MA (US)

( * ) Notice: Subject to any disclaimer, the term of this patent is extended or adjusted under 35 U.S.C. 154(b) by 379 days.

(21) Appl. No.: 17/934,301

(22) Filed: Sep. 22, 2022

(65) Prior Publication Data

US 2023/0091114 A1   Mar. 23, 2023

Related U.S. Application Data

(60) Provisional application No. 63/261,535, filed on Sep. 23, 2021.

(51) Int. Cl.
*A61B 17/32* (2006.01)
*A61B 17/00* (2006.01)

(52) U.S. Cl.
CPC .... *A61B 17/32* (2013.01); *A61B 2017/00398* (2013.01); *A61B 2017/0046* (2013.01); *A61B 2017/320004* (2013.01); *A61B 2017/320064* (2013.01)

(58) Field of Classification Search
None
See application file for complete search history.

(56) References Cited

U.S. PATENT DOCUMENTS

| | | | | |
|---|---|---|---|---|
| 5,213,913 | A * | 5/1993 | Anthony, III | B25F 5/02 292/87 |
| 5,910,152 | A * | 6/1999 | Bays | A61B 17/32002 606/174 |
| 2012/0078234 | A1 * | 3/2012 | Merchant | A61B 17/32002 604/542 |
| 2016/0235468 | A1 | 8/2016 | Prisco et al. | |
| 2020/0246020 | A1 * | 8/2020 | Magno | A61B 17/32002 |

* cited by examiner

*Primary Examiner* — Elizabeth Houston
*Assistant Examiner* — Lindsey Bachman
(74) *Attorney, Agent, or Firm* — Schwegman Lundberg & Woessner, P.A.

(57) ABSTRACT

A medical device may include a handpiece having a housing and a drive system arranged within the housing. The drive system may be adapted to operate a tool in direct contact with human matter of a patient at a treatment site. The device may also include a suction system integrated into the drive system and configured to remove human matter from the treatment site. The device may also include a motor removably attached to the housing and configured for delivering rotational power to the drive system while avoiding contact with the human matter.

18 Claims, 7 Drawing Sheets

MEDICAL DEVICE WITH REMOVABLE MOTOR

CROSS-REFERENCE TO RELATED APPLICATION

This application claims the benefit of priority to U.S. Provisional patent application Ser. No. 63/261,535, filed Sep. 23, 2021, the contents of which are hereby incorporated by reference in their entirety.

TECHNICAL FIELD

The present application is related to mechanized medical devices. More particularly, the present application is related to mechanized medical devices that deliver human matter, remove human matter, or exchange human matter such as tissues or fluids with a patient. Still more particularly, the present application is related to debridement devices or other human matter exchanging and mechanized medical devices having a disposable portion with a reusable power source.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Mechanized medical devices may be used for a variety of purposes in the medical device context. For example, motorized drills, saws, scalpels, debridement devices, or other mechanized devices may be used for a variety of respective purposes. Where these devices interact with bodily tissues or other human matter, either directly or indirectly, the devices may need to undergo a relatively involved reprocessing process to clean and sterilize the devices. In some situations, reprocessing may be relatively involved and rather than performing reprocessing, the device may be disposed of instead.

In some situations, separation of the portion of the device that has direct or indirect contact with the patient is relatively straight forward. That is, for example, a drill may include a removable drill bit where the drill bit has direct contact with the patient and the motorized portion has no direct or indirect contact with the patient. A saw, similarly, may have a removable saw blade, for example, where the saw blade has direct contact with the patient and the motorized portion has no direct or indirect interaction with the patient. However, some devices function to remove tissue, fluid, or other human matter from a patient and a larger portion of the device may be exposed to the patient's human matter. For example, a debridement device may have a portion of the device that directly interacts with unhealthy wound tissue by removing the tissue from the surface of the wound and another portion of the device that indirectly interacts with the unhealthy tissue by carrying the unhealthy tissue away for disposal. For example, a debridement device may include a suction portion that draws the unhealthy tissue into and through the device for disposal. In some cases, for purposes of slimline design or other purposes, the suction lumen may pass through the center of a cannulated motor, for example. While the disposable debrider blade or burr may be disposed of, the mechanized portion of the device may undergo costly reprocessing due to the internal exposure of the device to wound tissue and the relatively expensive nature of the device (e.g., prefer not to dispose). Avoiding reprocessing costs may be helpful to reduce cost for both the end user and the manufacturer.

SUMMARY

The following presents a simplified summary of one or more embodiments of the present disclosure in order to provide a basic understanding of such embodiments. This summary is not an extensive overview of all contemplated embodiments and is intended to neither identify key or critical elements of all embodiments, nor delineate the scope of any or all embodiments.

In one or more embodiments, a medical device may include a handpiece having a housing. The device may also include a drive system arranged within the housing and adapted to operate a device in direct contact with human matter of a patient at a treatment site. The device may also include a suction system integrated into the drive system and configured to remove human matter from the treatment site. The device may also have a motor removably attached to the housing and configured for delivering rotational power to the drive system while avoiding contact with the human matter.

In one or more embodiments, a debridement device may include a handpiece having a housing. The debridement device may also include a drive system arranged within the housing and adapted to operate a debridement device in direct contact with human matter of a patient at a debridement site. The debridement device may also include a suction system integrated into the drive system and configured to remove human matter from the debridement site. The debridement device may also include a motor removably attached to the housing and configured for delivering rotational power to the drive system while avoiding contact with the human matter.

In one or more embodiments, a method of using a medical device may include attaching a motor to a handpiece to engage the motor with a drive system of the handpiece. The method may also include powering the drive system with the motor to operate a device in direct contact with human matter of a patient at a treatment site. The method may also include removing human matter from the treatment site with a suction system integrated into the drive system. The method may also include removing and reusing the motor without reprocessing the motor.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

Figure 1:
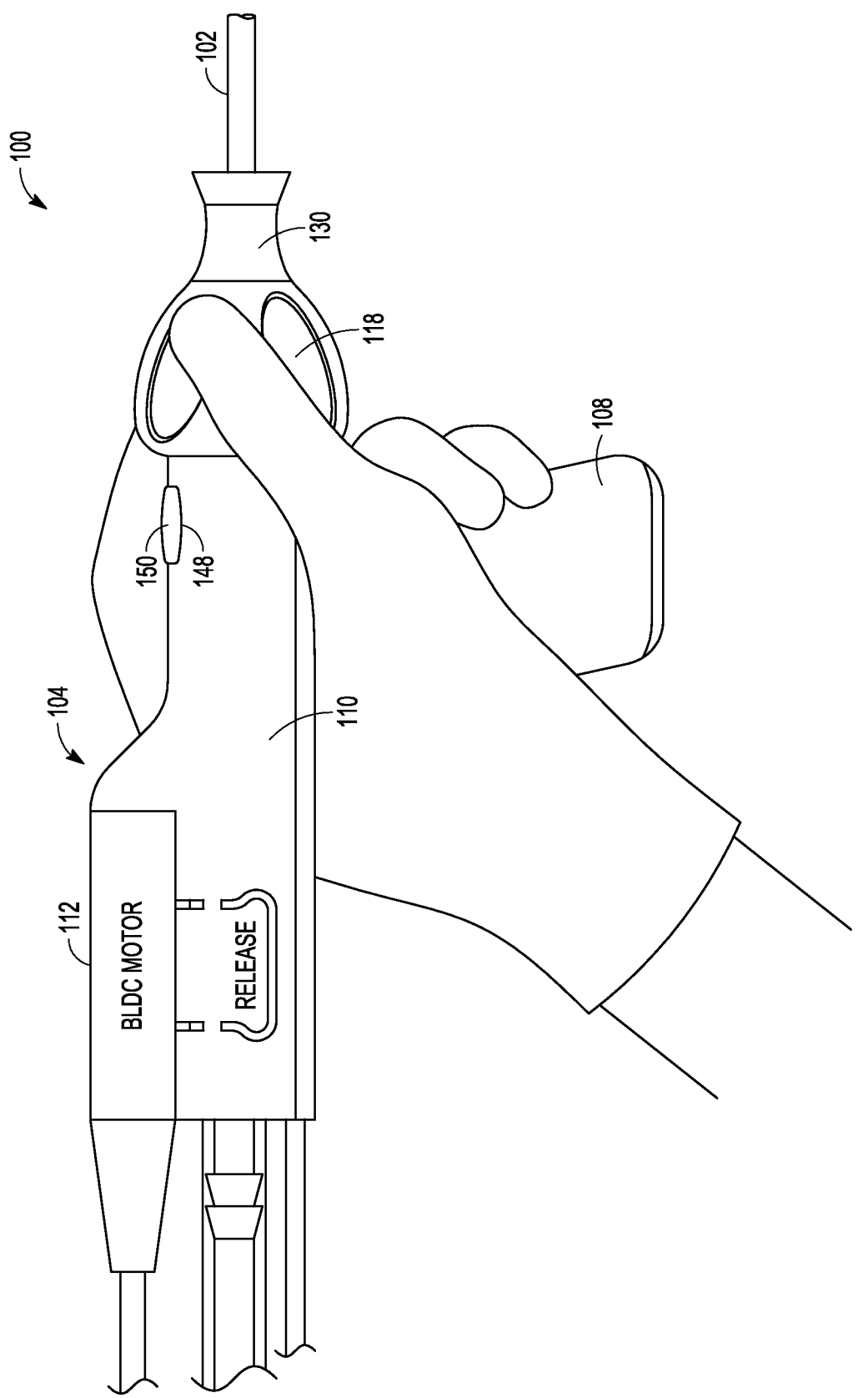
FIG. 1 is a perspective view of a medical device with a removable motor, according to one or more embodiments.

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present application relates to mechanized medical devices that have direct and/or indirect contact with patient tissues or fluids and, in particular, devices that have a suction component for removal of patient tissues or fluids. Debridement devices, for example, have direct contact with patient tissues and fluids when removing the tissues from the surgical site and indirect contact as the tissues and fluids are drawn through the device. The present application provides a removable motor for a mechanized medical device. Moreover, the motor is a non-cannulated motor that avoids indirect contact with human matter such as tissues and fluids, and, as such, avoids the need for reprocessing. This device, thus, reduces disposal and avoids reprocessing for at least a portion of the medical device, which reduces costs and disposal for the end user. Moreover, the design and development costs may be reduced by avoiding testing relating to reprocessing environments and conditions.

FIG. 1 is a perspective view of a medical device 100, according to one or more embodiments. In particular, the medical device 100 shown is a debridement device. The device may be adapted to resect unhealthy tissues from a surgical site on a patient and carry the resected unhealthy tissue away for disposal. While only partially shown, an outer tube 102 of the device may extend distally away from the handpiece 104 shown and may be adapted to hold, carry, or receive one of several different blades or burrs. For example, the outer tube 102 may be a detachable component allowing for use and replacement during and throughout a procedure, for example.

Figure 2:
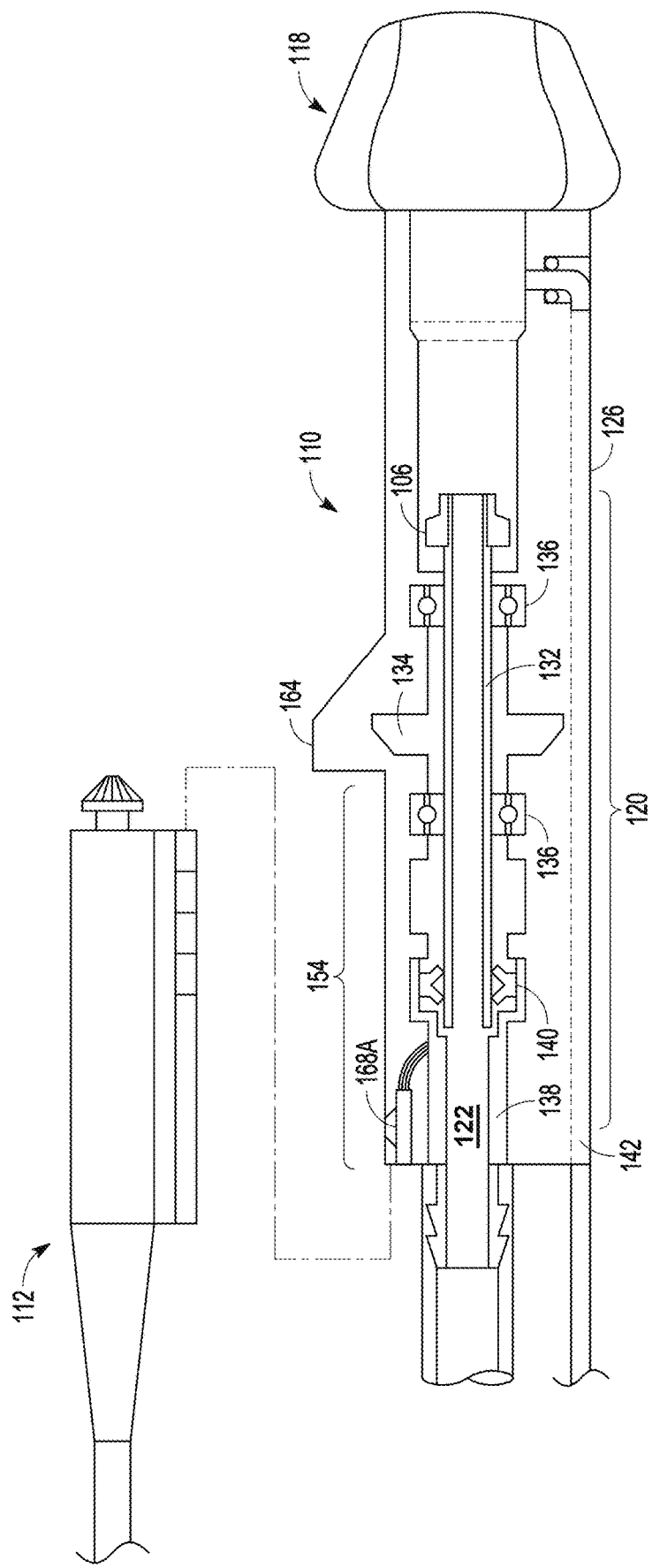
FIG. 2 is an exploded partial cross-sectional view thereof.

As partially shown further in FIG. 2, the outer tube 102 may be a substantially elongate cannulated element having a chamfered end for exposing the tip of a blade or burr arranged therein. That is, the blade or burr may include an elongate rod with a proximal or hub end and an opposite distal or working end. The rod may be arranged in and running through the outer tube 102 and the proximal end may extend into the handpiece 104 and securely engage a chuck 106 at an inner portion of an interface hub 130 for providing rotation to the blade or burr. The rod of the blade or burr may extend away from the inner portion of the interface hub 130 through the outer tube 102 to a working end that may be arranged at or around the chamfered end of the outer tube such that the working end is laterally exposed at the chamfered end. Suction may also be provided such that wound fluid and tissue or other human matter is drawn into the outer tube 102 and carried away from the wound through an annular space surrounding the rod within the outer tube 102. An interface hub 130 may provide the user with a portion to grasp to push an outer tube 102 onto the handpiece or remove an outer tube 102 from the handpiece 104. The outer tube 102 described above may be disposed of after one use or may be repeatedly used a plurality of times. In the case of repeated use, the blade may be reprocessed by the user or by a $3^{rd}$ party reprocessing company for example.

Turning now to the handpiece 104, the handpiece 104 may be adapted to provide a base component for attachment and detachment of the outer tube and may also provide operational power and suction to the outer tube 102. As show in FIG. 1, the handpiece 104 of the device may include a grip 108, a body portion 110, and a power source 112.

The grip 108 may extend from the body portion and be adapted for grasping by the user to control the device 100. As shown, in one or more embodiments, the grip 108 may be a pistol grip, for example. The pistol grip may include a generally rectangular or trapezoidal shape when viewed from the side that may extend generally downward from the body portion 110. The grip 108 may include radiused corners around its periphery for a more comfortable and ergonomic grip. In one or more embodiments, the grip 108 may be a reverse pistol grip, which extends slightly forward as it extends downward. In one or more embodiments, the grip 108 may be a reusable grip 108 that slidingly engages a pair of rails 116 on a bottom of the body portion 110 as shown in FIG. 4B, for example. That is, the grip (not shown in FIG. 4B) may include a groove or channel extending longitudinally and on a top surface thereof. The groove or channel may include inwardly protruding rails near the top of the groove or channel that may be adapted to engage grooves 114 extending along the sides and near the bottom of the housing 126 as shown in FIG. 4B. The grip 108 may be slidingly attached to the bottom of the body portion 110 for a procedure and removed from the body portion 110 after the procedure. Since no direct or indirect contact with bodily fluids may occur with the grip 108, the grip 108 may be reused without reprocessing and, instead, may more simply be wiped down and/or washed between procedures. In one or more embodiments, the grip 108 may include a collapsible handle such as that shown and described in U.S. Provisional Application No. 63/147,728 entitled Collapsible Handle Design for Debriders and filed on Feb. 9, 2021, the content of which is hereby incorporated by reference herein in its entirety.

Referring now to FIGS. 2 and 4A-4C, the body portion 110 of the handpiece 104 may be described. The body portion 110 may be configured to house several of the working components of the device and may provide one or more pathways for the removal of human matter from a patient and/or pathways for delivery of irrigating fluids. The body portion 110 may also provide for attachment of additional components such as the grip 108 described above and/or a reusable motor or other power source 112, described below. Moreover, the body portion 110 may function together with the grip 108 to allow a user to hold the device and perform a procedure. As shown, the body portion 110 of the handpiece 104 may include a nosecone 118, a drive system 120, a suction system 122, an irrigation system 124, a housing 126, and a communication/control system 128. Each of these portions of the body portion may be described in turn.

The nosecone 118 may be arranged on a distal end of the handpiece 104 and may be adapted to close off the distal end and to receive one of more different tool types. In one or more embodiments, as shown in FIG. 1 and again in FIG. 5, the nosecone 118 may be adapted to receive the interface hub 130, which may be inserted into the nosecone 118 and sealing engage the handpiece 104. The nosecone 118 may provide a grasping surface, for example, where a user may grasp the nosecone 118 and the interface hub 130 on the outer tube and push or pull particular outer tube attachments on or off of the handpiece. In one or more embodiments, the interface hub 130, nosecone 118, and/or other related elements may be the same or similar to those described in U.S. patent application Ser. No. 17/010,026 entitled Detachable Handheld Tissue Removal Device and filed on Sep. 2, 2020, the content of which is hereby incorporated by reference herein in its entirety.

The drive system 120 may be arranged within the housing 126 behind the nosecone 118 and may be adapted to provide rotational power to a tool, such as a blade or burr, arranged on the distal end of the handpiece 104. As shown, the drive system 120 may include a driveshaft 132 driven by a gear, belt, chain, or other rotational power transfer element 134. In one or more embodiments, the rotational power transfer element 134 may include a bevel gear that is overmolded on the drive shaft 132, for example. As shown, the driveshaft 132 may be arranged within the housing 126 and supported by a series of bearing or bushings 136 so as to hold the driveshaft 132 in place, but allow the driveshaft 132 to rotate under the rotational drive force provided by the rotational power transfer element 134. The driveshaft 132 may be a generally hollow elongate element to allow for the driveshaft 132 to be a part of the suction system 122 described in more detail below. As shown, the driveshaft 132 may extend longitudinally within the housing 126 from a suction fitting 138 at a proximal end of the housing 126 to a chuck or other tool engaging feature 106 at a distal end. The proximal end of the driveshaft 132 may be arranged within a seal 140 at the suction fitting 138. The chuck 106 at the distal end of the driveshaft 132 may be arranged in a connection cavity arranged behind the nose cone 118, for example. As mentioned above, the chuck 106 may be adapted to receive a proximal end of an inner portion of the interface hub 130 of a disposable tool such as a blade or burr. The chuck 106 may have a hexagonal internal shape, a square internal shape, or another shaped adapted to receive the proximal end of the inner portion of the interface hub 130 and transfer rotational power to the hub 130.

Figure 5:
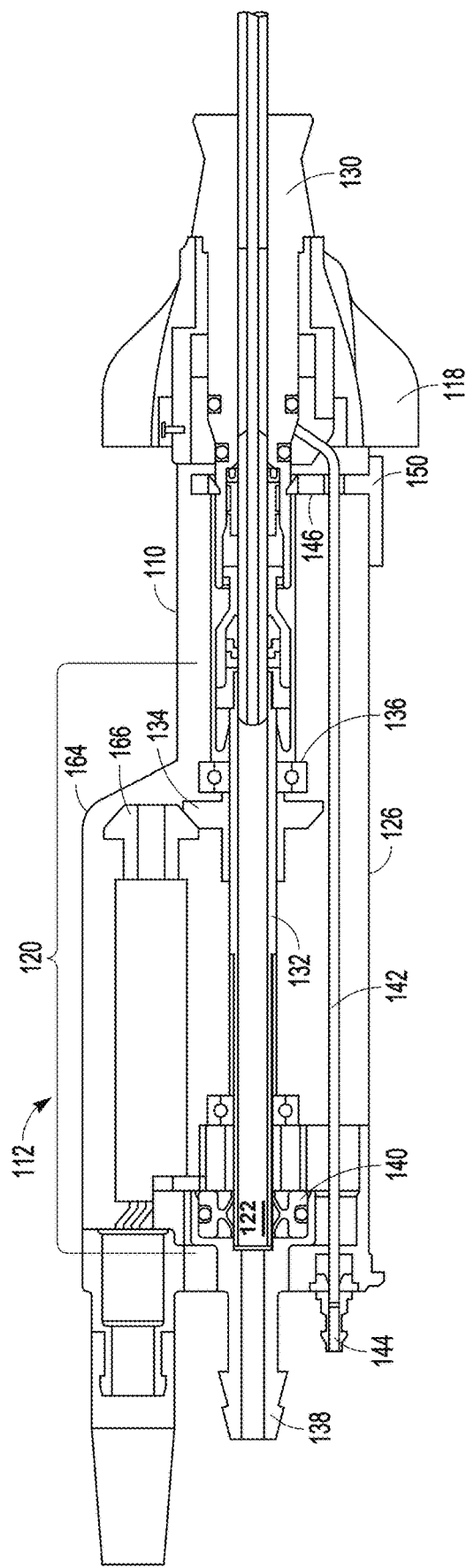
FIG. 5 is a cross-section view of an adaptation of the above system to an existing reusable handpiece.

The suction system 122 may include a hollow lumen formed on the inside of the driveshaft 132 and, as such, the suction system may be integrated into the drive system 120. A suction fitting 138 mentioned above may be arranged on a proximal end of the device. The suction fitting 138 may include an external hose barb, for example, allowing for the attachment of tubing to the proximal end of the handpiece 104 and, as such, a vacuum pump or other suction device may be secured to the handpiece to provide suction. The suction fitting 138 may extend distally into the proximal end of the handpiece and sealingly receive the proximal end of the driveshaft 132. In addition, and as best shown in FIG. 5, the distal end of the driveshaft 132 may engage additional sealing components that place the internal lumen of the driveshaft 132 in fluid communication with the internal lumen of the interface hub 130 thereby establishing a continuous lumen from the tip of the interface hub 130 to the back side of the handpiece 104.

The irrigation system 124 may similarly extend from a proximal end of the handpiece 110 to a distal end. In one or more embodiments, the irrigation system 124 may include an internal conduit 142 extending along an internal bottom side of the handpiece 104 from a fluid fitting 144 at a proximal end up to the nosecone 118, for example. As shown, the internal conduit 142 may be a generally uninterrupted tube, for example, that may carry fluid from a fitting 144 at the proximal end of the handpiece to a distal end. The fitting 144 at the proximal end may sealingly engage the conduit 142 with one or more surrounding seals and may include a hose barb or other fluid line connecting element allowing for an irrigation fluid supply line to be connected.

The housing 126 may form a containing envelope around the inner operating elements of the body portion 110 such as the drive system 120, suction system 122, and the irrigation system 124. The housing 126 may include a substantially solid outer wall surrounding all or a portion of these systems. The housing 126 may be shaped to enclose all or a part of these systems, be handleable by a human hand, and be adapted to engage the grip 108 and the reusable power source or motor 112. As shown in FIG. 2, the housing 126 may include a generally elongate and cylindrical housing having a longitudinal axis. The housing 126 may be adapted to receive the nosecone 118 on a distal end thereof and may have a generally open distal end. In one or more embodiments, as shown in FIG. 5, the interface hub 130 may extend through the nosecone 118 and into the housing 126 and a securing lock 146 may traverse the cross-section of the housing 126 to engage the interface hub 130. For this purpose, the housing 126 may include an opening 148 on an upper surface for positioning of a button 150 on the securing lock 146. In one or more embodiments, the button 150 and associated opening 148 in the housing 126 may be arranged on the top of the housing 126 as shown in FIG. 1 or, alternatively, on the bottom as shown in FIG. 5. On a proximal end of the housing 126, the housing 126 may include an opening for the suction fitting 138 and an opening for the irrigation fitting 144.

The housing 126 may also include a grip interface on a bottom surface thereof. As mentioned with respect to the grip 108, and as shown in FIG. 4B, the grip interface on the housing may include a generally protruding element 152 on a bottom surface of the housing 126 having a pair of outwardly flaring rails 116. The rails 116 may extend longitudinally along the bottom surface of the housing and define a pair of longitudinally extending grooves 114 above the rails 116. Corresponding rails near the top of the channel on the grip 108, discussed above, may engage the grooves 114 and slidingly engage the bottom of the housing 126 at the grip interface. In some embodiments, the grooves 114 may include a stop near a distal portion of the housing 126 defining a forward most position of the grip 108 relative to the housing 126. In other embodiments, a detent, catch, or other retaining element may be provided along the slide path of the grip 108 on the grip 108 and/or on the grip interface of the housing 126.

In a similar fashion, the housing may also include a motor-engaging interface. As shown in FIG. 2, the motor-engaging interface 154 may be arranged on an upper and rear surface of the housing 126 and is shown in cross-section in FIG. 4B. As shown, the housing 126 may include a channel 156 extending into the top surface of the housing and extending longitudinally along the length of the housing 126. The sidewalls of the channel may extend upwardly from a generally flat or slightly convex bottom surface 158 and may turn inwardly at the top of the channel 156 to form a pair of rails 160 extending along the channel 156. The channel 156 may, thus, be adapted to slidingly receive a protruding and oppositely shaped element 162 on a bottom of the motor 112 described in more detail below. At a distal end of the motor-engaging interface 154, the housing 126 may include a hood 164 that may function as a stop for the slidingly engaging motor 112 and a mechanical access port for engagement of the drive system 120 by the motor 112. That is, as shown, the hood 164 may be arranged generally above the drive gear or rotational power transfer element 134 of the drive system 120. The hood 164 may be generally open on a proximal side thereof to allow a drive element 166 on the motor 122 to engage the rotational power transfer element 134 on the drive system 120. As shown in FIG. 5, for example, a bevel pinion gear 166 on a distal end of the motor 112 may engage a bevel gear 134 on the driveshaft 132 to transfer power from the motor 112 to the driveshaft 132.

The communication/control system 128 may be adapted to provide control signals to the motor. For example, and as shown in FIG. 2, one or more electrical contacts 168A, may be arranged on an upper rear portion of the housing 126 within the motor-engaging interface 154. The contacts 168A may be adapted to contact similar contacts 168B on the motor assembly 112 allowing for control signals to be communicated to the motor. That is, for example, the controller of the device may include an RFID antenna that energizes a passive RFID tag on the one or more outer tube portions 102. Depending on the outer tube 102 that is attached, the controller may send particular speed signals to the motor to operate at a speed suitable for the particular outer tube 102 that is attached. For example, a blade may be run at approximately 5000 RPM and in oscillating mode, while a burr may be run closer to 15,000 RPM in a single direction. In one or more embodiments, a particular outer tube may be considered attached when it is in close proximity to the handpiece and in other examples, the controller may be able to tell if the outer tube if fully engaged or present. Still other approaches to determining which control signals to send to the motor may be provided.

The housing 126 may also include a motor latch 184 for securing the motor in place on the housing 126. That is, while the sliding engagement of the motor 112 onto the housing 126 may generally secure the motor 112 to the housing 126, it might not be sufficient to hold the motor 112 in an engaged relationship with the rotational power transfer element 134 of the drive system 120. For this purpose, a motor latch 184 may be provided. For purposes of describing the latch 184, further details of the motor may first be provided.

Having described the several parts of the body portion 110 including the nosecone 118, the drive system 120, the suction system 122, the irrigation system 124, the housing 126, and the communication/control system 128, it may be appreciated that this body portion 110 may be a disposable component. That is, the grip 108 and the motor 112 may be removed from the body portion after a procedure allowing each of those devices to be wiped down and easily cleaned and/or disinfected for reuse and the body portion may be disposed. As such, the body portion 110 may be made from relatively inexpensive materials including plastics or other relatively strong, but inexpensive materials. Moreover, the body portion may be generally free of metals that may be well suited for computing components such as heavy metals or expensive metals. Still other factors may be considered in manufacturing the disposable body portion.

The motor 112 may be adapted to provide rotational power to the handpiece 104 and may be further adapted for removable engagement with the handpiece 104 so as to be reusable. That is, the arrangement of the motor 112 may be such that the motor does not come into direct or indirect contact with bodily tissues, fluids, or other human matter during a debridement or other procedure. As such, the motor 112 may be detached from the handpiece 104 after use and may be wiped down or cleaned, but without the need for reprocessing steps. In one or more embodiments, for example, the motor 112 may be a non-cannulated motor that is not arranged at or near the suction system 122 and, as such, bodily tissues, fluids, or other human matter may avoid flowing through the motor 112. More particularly, the motor 112 may be arranged eccentrically or offset from the driveshaft 132 of the body portion 110 and the drive element 166 together with the rotational power transfer element 134 of the driveshaft 132 may function to translate the rotation power of the motor 112 downward into the housing 126 and in line with the driveshaft 132 and tools extending therefrom. In one or more embodiments, the longitudinal axis of the motor 112 may be parallel to, but offset from, the longitudinal axis of the driveshaft 132 as shown. However, the longitudinal axis of the motor 112 may also be skewed or non-parallel with the longitudinal axis of the driveshaft 132 and, in one or more embodiments, the longitudinal axis of the motor 112 may be orthogonal to the longitudinal axis of the driveshaft 132. Gearing or other rotational power transfer devices may be used to reorient the rotational power provide by the motor 112.

Figure 3A:
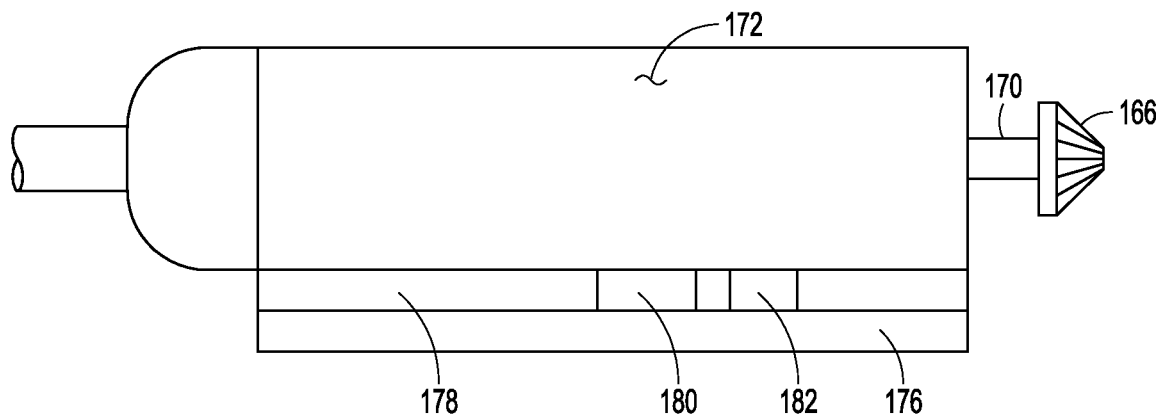
FIG. 3A is a side view of the removable motor, according to one or more embodiments.
Figure 3B:
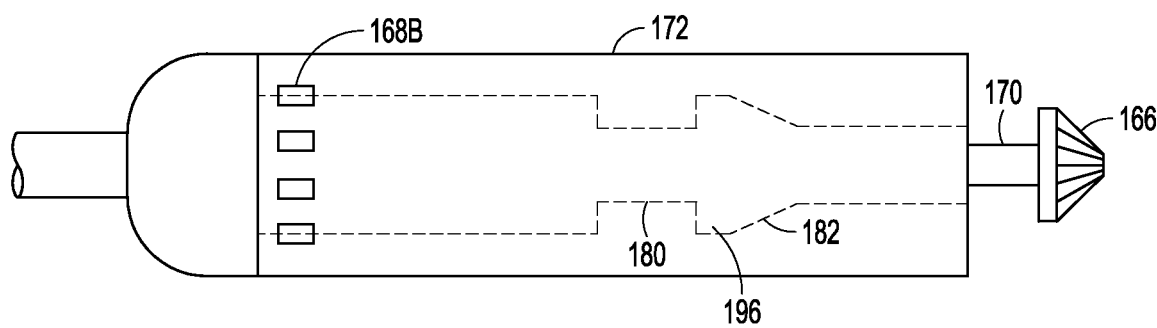
FIG. 3B is a bottom view thereof.
Figure 3C:
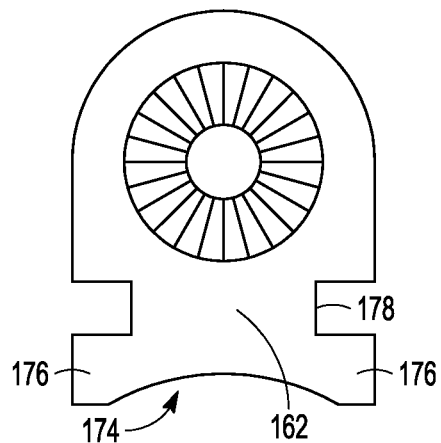
FIG. 3C is a front view thereof.

As shown in FIGS. 3A-3C, the motor 112 may include a corded motor such as a brushless DC motor. While a corded motor is shown, a battery powered motor may also be provided. The motor 112 may include a motor shaft 170 extending distally from the motor 112 to a drive element 166. The drive element 166 may be in the form of a bevel pinion gear or other gear as shown. In one or more other embodiments, a drive pulley, sprocket, or other rotational drive element may be provided. The motor 112 may also include a motor housing 172 configured for engagement with the motor-engaging interface 154 of the housing 126 of the handpiece 104. As shown in FIG. 3C, a sliding engagement element may be provided on the bottom side of the motor housing 172. As shown, the sliding engagement element may include a downwardly protruding element 162 that extends longitudinally along the length of the motor housing 172. The downwardly protruding element 162 may include a pair of laterally extending rails 176 on opposing bottom edges forming a pair of grooves 178 above the rails. The bottom surface 174 of the downwardly protruding element may be flat or, as shown, may be slightly concave and adapted to align and engage the convex surface 158 on the bottom of the channel 156 in the motor-engaging interface 154 of the housing 126. As shown in FIG. 4B, the motor may, thus, slidingly engage the motor-engaging interface 154 on the housing 126 to secure the motor 112 to the housing 126. As the motor 112 is slid from a proximal entry position on the housing to a distal position, the drive element 166 on the distal end of the motor 122 may enter the hood 164 on the housing 126 and engage the rotational power transfer element 134 on the drive system 120 of the body portion 110.

The bottom view of the motor is shown in FIG. 3B. As shown, the bottom of the motor housing may include RFID contacts or other contacts 168B for contacting corresponding contacts arranged in the motor-engaging interface 154 as discussed above. Moreover, and as shown, the grooves 178 above the rails 176 of the motor housing 172 may each include notch 180 arranged along a length of the groove 178. Each groove 178 may also include wedge portion 182 arranged distal to the notch 180. The notch 180 and wedge portions 182 may be adapted to assist with engagement of a latch 184 on the housing 126 discussed in more detail below.

Figure 4A:
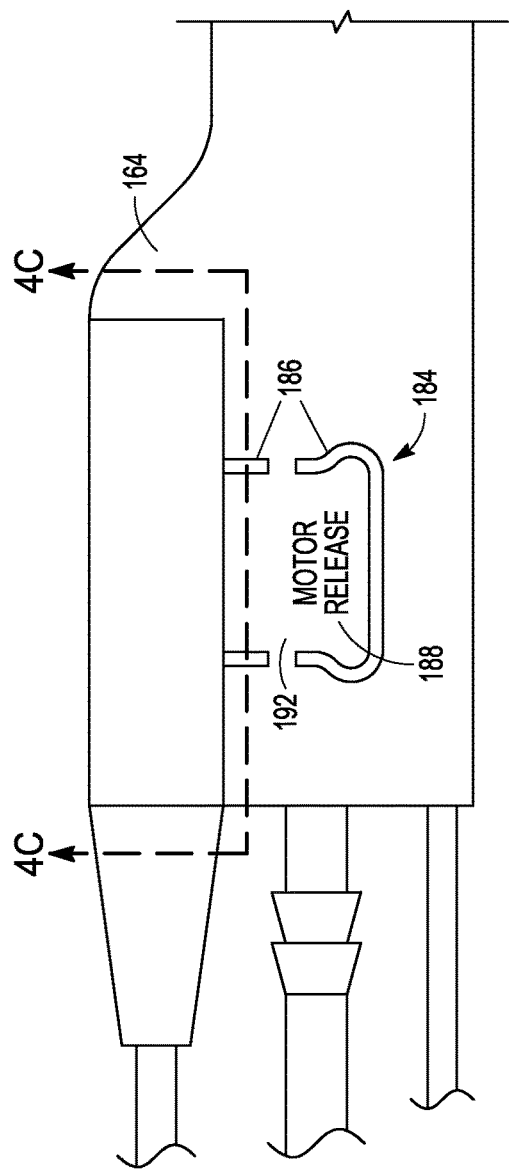
FIG. 4A is a side view of a connection of the removable motor to a body of the medical device.
Figure 4B:
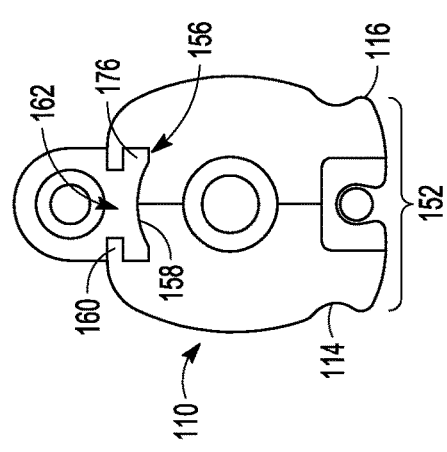
FIG. 4B is a rear view thereof.
Figure 4C:
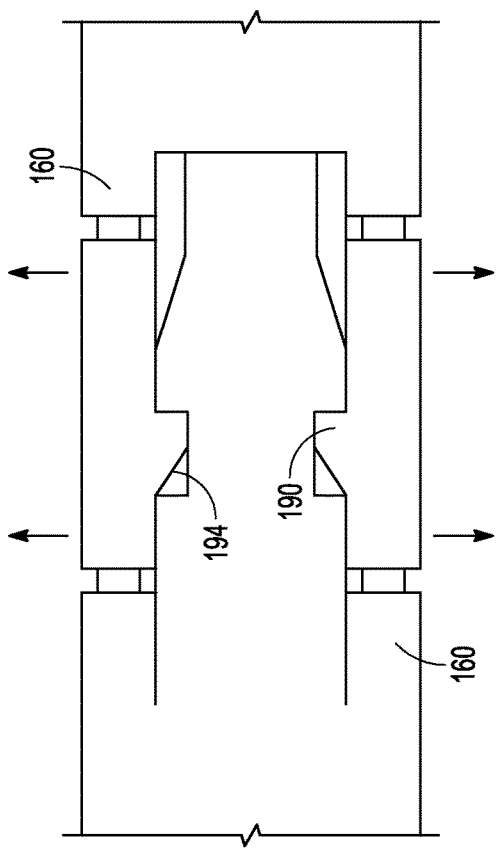
FIG. 4C is a cross-section view thereof.
Figure 4D:
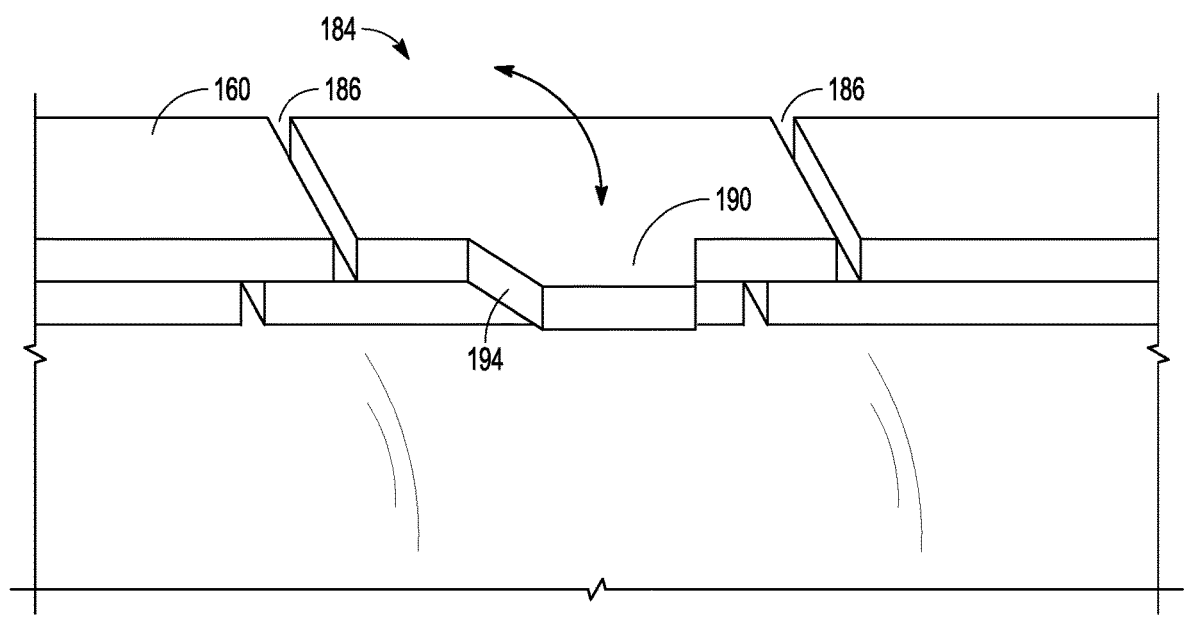
FIG. 4D is a perspective view of a motor latch thereof.

With reference to FIGS. 4A, 4B, and FIG. 3B, a description of the latch 184 may be provided. As mentioned, the latch 184 may be adapted to secure the motor 112 to the housing 126 of the body portion 110 and maintain the drive element 166 of the motor 112 in engagement with the drive system 120 of the body portion 110 unless/until the motor 112 is released from the housing 126. As shown in FIG. 4A, the side of the housing 126 may include cutouts 186 extending through the sidewall of the housing 126 and defining a motor release mechanism. As shown, the cutouts 186 may include a generally u-shaped cutout arranged at or near a mid-height of the housing 126 and defining a release button 188 and a locking tab 190. That is, the legs of the u-shaped cutout may extend upward along the sides of the housing 126 to the top of the housing 126 and through the rails 160 on either side of the channel 156 in the motor-engaging interface 154. The legs of the u-shaped cutout may be interrupted at or near a midpoint of the leg height. In one or more embodiments, the interruption may be located at a position to align with the intersection of the bottom 158 of the channel 156 of the motor-engaging housing 154 and the outer wall of the housing 126. At this location, the housing 126 wall may be continuous across the cutout forming a living hinge 192, for example. As shown in FIG. 4C, the rails 160 of the channel 156 on the motor-engaging interface 154 may include an inwardly extending tab 190 with a sloped proximal surface 194. That is, and as shown in perspective view in FIG. 4D, the tab 190 may extend further into and across the top of the channel 156 than the rails 160 themselves and a proximal side of the tab may have a sloped or chamfered surface 194 adapted for engaging the wedge portion 182 on the motor 112. As the motor 112 is slid along the motor-engaging interface 154 of the housing 126, the wedge portion 182 of the grooves 178 may reach the sloped proximal surface 194 of the inwardly extending tabs 190 on the rails 160 of the channel 156. As the motor is advanced distally, the interacting sloping surface (e.g., the wedge portions 182 on the motor 112 and the sloped surface 194 on the tabs 190 may force the tabs 190 outwardly causing rotation of the tab portion of the rails 160 to pivot outwardly about the living hinge 192 as shown in FIGS. 4C and 4D. As the motor 112 is further advanced in a distal direction, the tabs 190 may be forced fully outward and may ride along the plateau surface 196 proximal to the wedge portions 182 on the grooves 178 of the motor 112. When the motor 112 is advance fully distally, the tabs 190 may spring into the notches 180 in the grooves 178 on the motor 112 due to the energy stored in the living hinge 192. This may cause the distal surface of the tabs 190 to engage a distal surface of the notch 180 thereby holding the motor 112 in place unless and until the tabs are released. The tabs 190 may be released by pressing on the release button 188 on each side of the housing 126 causing the tabs 190 to rotate about the living hinge 192 and out of the notches 180 in the grooves 178 of the motor 112 allowing the motor 112 to be slid proximally and detached from the body portion 110.

It is to be appreciated that while the latch 184 has been described as being an interaction of a tab 190 on an upper end of the latch 184 with a notch 180 in a groove on the motor housing, the latch 184 may also be a notch on the rail 176 and a tab below the rail 160. That is, while the latch is shown as being in plane with the groove 178, it may instead or additionally be in plane with the rail 176. Still other approaches to providing a latching mechanism may be provided.

It is to be appreciated that while sliding engagement of the motor 112 and grip 108 have been described, other types of removable engagement may be provided. For example, the motor 112 or grip 108 may include tabs on a bottom/front edge that engage pockets in the housing and the back end of the motor/grip may include a latch to the housing. In this embodiment, the motor or grip may be tipped downward from back to front to engage the tabs on the front of the motor/grip with the housing and then the back end of the motor/grip may be pivoted downward about the front edge to engage the latch on the back of the motor/grip. A similar approach may be used from side-to-side, for example instead of front to back. In still other embodiments, a strap or latching strap may extend over and/or around the motor or grip to secure it to the housing. Lugs and pockets or other motor/grip/housing features may be used resist slipping or moving of the motor within the strap. In still other embodiments, a snap fit may be provided where the motor or grip snaps onto a respective interface. For example, a latch similar to the one described with a living hinge may be provided where pressing the motor or grip toward housing causes the latches to pivot outward and then snap into place when the motor or grip fully engaged. Still other approaches to removable attaching the motor 112 or grip 108 may be provided.

It is to be appreciated that the present motor 112, and grip 108 for that matter, may be removed from the handpiece without the use of tools or other devices. That is, removable in this context means that the respective device may be removed without the use of tools. For example, the present device may not require the removal of any screws, bolts, or other tool adapted fasteners. Moreover, the presently described motor may be reusable and reusable in this context is more than a mere ability to use the device again, but also means that the device can be used again without reprocessing. That is, in particular, the removable and reusable motor of the present application has been designed to avoid direct or indirect contact with bodily tissues, fluids, or other human matter and, as such, may be reused without being reprocessed, which may otherwise involve extensive cleaning and sterilization processes such as harsh chemical cleaning, autoclaving, and the like. Instead, the present reusable motor may more simply be wiped down and stored for reuse.

The above-described device may be advantageous by isolating a relatively expensive component of the system (e.g., the power source or motor) from a disposable portion (e.g., the body portion) and allowing the device (e.g., the power source or motor) to be reused without the need for reprocessing. It is to be appreciate that reprocessing may take time and cost money for medical systems, which may make it more cost-effective to dispose of a device and purchase a new one rather than spend the time and money on reprocessing. Moreover, reprocessable components may require a more involved design, development, and testing process because the reprocessable devices may need to withstand more cycles of use in addition to relatively arduous (e.g., chemical exposures and/or high heat exposures) and repeating reprocessing. On the other hand, disposable devices may remain expensive and disposal may be wasteful. As such, the present application presents a system that avoids both disposal and reprocessing of selected components and, as such, benefits both the manufacturer and the end user.

Figure 6:
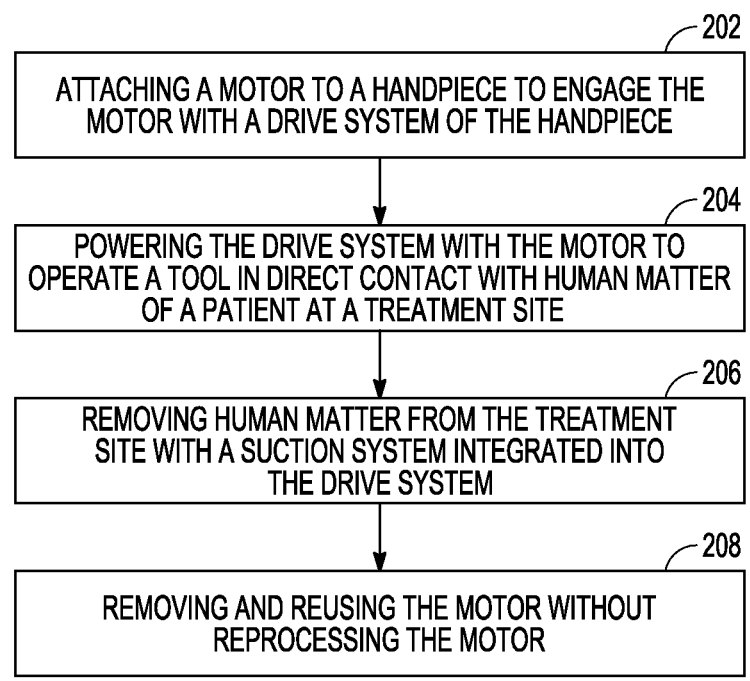
FIG. 6 is a diagram depicting a method of using a medical device, according to one or more embodiments.

In operation and use, and as shown in FIG. 6, the medical device may be used to perform a method of treating a patient 200. In one or more embodiments, the method may include attaching a motor to a handpiece to engage the motor with a drive system of the handpiece 202. For example, the motor may include a motor housing and the attaching the motor to a handpiece may include slidingly engaging the motor onto the housing and advancing the motor distally until it engages a latch. In advancing the motor distally, a drive element of the motor may engage a rotational power transfer element on the drive system of the handpiece. It is to be appreciated that the beveled nature of the drive element and the rotational power transfer element may be well suited for longitudinally engaging the two elements. That is, the sliding motion of one beveled gear toward another beveled gear may cause the gears to naturally engage one another and naturally rotate into position so the gear teeth fully engage without the need for manually rotating one or the other. The method may also include powering the drive system with the motor to operate a tool in direct contact with human matter of a patient at a treatment site 204. For example, in the case of a debridement device, the motor may rotate a drive shaft of the drive system, which may, in turn, rotate a blade or burr tool extending along an outer tube of the device. The method may also include removing human matter from the treatment site with a suction system integrated into the drive system 206. That is, and again in the case of a debridement device, the suction system may be integrated into the drive system by way of a lumen extending through the drive shaft. Removing human matter from the treatment site may include operating a vacuum pump or other suction device to establish suction in the outer tube, draw the human matter into the outer tube and into and through the drive shaft to a suction fitting on a proximal end of the handpiece and out the suction tubing. The method may also include removing and reusing the motor without reprocessing the motor 208. That is, once the procedure is complete, the motor may be removed from the handpiece by, for example, depressing the release buttons on either side of the housing causing the latch to disengage the motor and allow the motor to slide proximally and off of the housing of the handpiece. Since use of the motor does not cause it to come into direct or indirect contact with the human matter, the motor may be reused without reprocessing the motor. For example, the motor may be wiped down or otherwise easily cleaned and disinfected without autoclaving, using harsh chemicals, or otherwise performing other reprocessing steps.

The directional descriptors described herein are used with their normal and customary use in the art. For example, proximal, distal, lateral, up, down, top and bottom may be used to describe the apparatus with the longitudinal axis arranged parallel to a ground with the device in an upright position. The proximal direction refers to a direction towards the user end of the apparatus, and the distal direction represents a direction towards the patient end of the apparatus.

Relative terms described herein, such as, "about" or "substantially" may be used to indicate a possible variation of ±10% in a stated numeric value, or a manufacturing variation.

As described throughout this disclosure, components and assemblies can be operably connected to each other and interact with one another in a manner that provides improved actuation, a more compact and simpler design, lower cost, and better user satisfaction than traditional medical devices.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical device, comprising:
   a handpiece having a housing;
   a drive system arranged at least partially within the housing and adapted to operate a tool configured for contact with human matter of a patient at a treatment site, the drive system comprising a drive shaft having a first gear arranged thereon;
   a suction system integrated into the drive system and configured to remove human matter from the treatment site; and
   a motor removably attachable to the housing and configured for delivering rotational power to the drive system while avoiding contact with the human matter, the motor comprising a motor shaft and a second gear, wherein the second gear is arranged on a distal end thereof and configured for direct rotational engagement with the first gear when the motor is attached to the housing.

2. The medical device of claim 1, wherein the suction system is integrated into the drive system by way of a lumen extending through the drive shaft.

3. The medical device of claim 1, wherein the motor is eccentrically arranged relative to the drive shaft.

4. The medical device of claim 1, wherein the first gear comprises a bevel pinion gear and the second gear comprises a bevel drive gear.

5. The medical device of claim 4, wherein the bevel drive gear is concentrically arranged on the drive shaft.

6. The medical device of claim 1, wherein the motor is a non-cannulated motor.

7. The medical device of claim 1, wherein the housing comprises a motor-engaging interface having a channel with rails and the motor comprises a protruding element with rails and grooves adapted to slidingly engage the channel.

8. The medical device of claim 7, wherein the housing comprises a motor latch for securing the motor in position along the motor-engaging interface.

9. The medical device of claim 8, wherein the motor latch comprises one or more cutouts on a sidewall thereof defining a release button and a living hinge.

10. The medical device of claim 9, wherein the motor latch further comprises an inwardly extending tab on each of the rails of the channel.

11. The medical device of claim 10, wherein the grooves of the protruding element of the motor each comprise a notch for engaging respective inwardly extending tabs on the rails of the channel.

12. The medical device of claim 11, wherein a bottom of the channel comprises a convex surface and a bottom surface of the protruding element comprise a corresponding concave surface.

13. The medical device of claim 12, further comprising a removable and reusable grip.

14. A debridement device, comprising:
    a handpiece having a housing;
    a drive system arranged within the housing and adapted to operate a debridement tool configured for contact with human matter of a patient at a debridement site, the drive system comprising a drive shaft having a first gear arranged thereon;
    a suction system integrated into the drive system and configured to remove human matter from the debridement site; and
    a motor removably attachable to the housing and configured for delivering rotational power to the drive system while avoiding contact with the human matter, the motor comprising a motor shaft and a second gear, wherein the second gear is arranged on a distal end thereof and configured for direct rotational engagement with the first gear when the motor is attached to the housing.

15. The debridement device of claim 14, wherein the debridement tool is a blade or burr.

16. The debridement device of claim 14, wherein the debridement tool comprises an outer tube extending distally from the handpiece and the tool is arranged in the outer tube.

17. A method of using a medical device, comprising:
    attaching a motor to a handpiece to engage the motor with a drive system of the handpiece, the drive system having a drive shaft with a first gear thereon and the motor comprising motor shaft and a second gear, wherein the second gear is arranged on a distal end thereof and configured for direct rotational engagement with the first gear when the motor is attached to the handpiece;
    powering the drive system with the motor to operate a tool in direct contact with human matter of a patient at a treatment site;
    removing human matter from the treatment site with a suction system integrated into the drive system; and
    removing and reusing the motor without reprocessing the motor.

18. The method of claim 17, wherein removing the motor from the handpiece comprises pressing a release button on the handpiece and slidingly removing the motor from the handpiece.

* * * * *